United States Patent [19]
Von Weissenfluh et al.

[11] Patent Number: 5,626,475
[45] Date of Patent: May 6, 1997

[54] DENTAL MATRIX TENSIONER

[75] Inventors: Hans Von Weissenfluh, Magadino; Beat Von Weissenfluh, Gentilino, both of Switzerland

[73] Assignee: Hawe-Neos Dental Dr. H. Von Weissenfluh S.A., Bioggio, Switzerland

[21] Appl. No.: 256,010
[22] PCT Filed: Oct. 25, 1993
[86] PCT No.: PCT/EP93/02940
§ 371 Date: Jun. 20, 1994
§ 102(e) Date: Jun. 20, 1994
[87] PCT Pub. No.: WO94/09716
PCT Pub. Date: May 11, 1994

[30] Foreign Application Priority Data

Oct. 28, 1992 [CH] Switzerland .............. 3366/92
Oct. 5, 1993 [CH] Switzerland .............. 2989/93

[51] Int. Cl.$^6$ ........................... A61C 5/04
[52] U.S. Cl. ........................... 433/155; 433/39
[58] Field of Search ............... 433/44, 45, 153, 433/154, 155, 39, 40

[56] References Cited

U.S. PATENT DOCUMENTS

| | | |
|---|---|---|
| 1,202,698 | 10/1916 | Ford .......................... 433/142 |
| 1,359,665 | 11/1920 | Borkin . |
| 2,995,822 | 8/1961 | Tofflemire . |
| 4,202,103 | 5/1980 | Zall et al. . |
| 4,396,374 | 8/1983 | Ericson . |
| 4,915,627 | 4/1990 | Hirdes ....................... 433/155 |
| 5,055,045 | 10/1991 | Dickie et al. ................ 433/155 |
| 5,342,197 | 8/1994 | Stein et al. ................. 433/155 |

FOREIGN PATENT DOCUMENTS

| | | | |
|---|---|---|---|
| 3907338 | 2/1990 | Germany ........................ 433/155 |
| 3913309 | 10/1990 | Germany . |
| 15762 | of 1913 | United Kingdom . |

*Primary Examiner*—Ren Yan
*Attorney, Agent, or Firm*—Young & Thompson

[57] ABSTRACT

A dental matrix tensioner has a casing containing a pin rotatable relative to the casing, the pin having a slot therein for releasably receiving a dental matrix and for tightening the matrix about a tooth upon rotation of the pin relative to the casing. A device to rotate the pin relative to the casing comprises an elongated assembly, and a member slidable lengthwise of the assembly in one direction to grip external portions of the casing and in an opposite direction to release those external portions of casing thereby selectively releasably to retain the rotating device in assembled relation with the casing. The lengthwise slidable member is also rotatable and is selectively engageable with the pin to rotate the pin upon rotation of the slidable member. The slidable and rotatable member has a noncircular end which fits removably in a noncircular recess in the pin whereupon when that end is inserted in the noncircular recess and sliding member is rotated, the pin is turned relative to the casing.

7 Claims, 5 Drawing Sheets

DENTAL MATRIX TENSIONER

FIELD OF THE INVENTION

The invention relates to the field of devices for the application and the tightening of matrices for dental reconstructions in odontology.

BACKGROUND OF THE INVENTION

Among such devices, the most advanced to date include a matrix tightener comprising a turning pin attached to a casing within which the pin itself pulls the matrix in its rotation, placing it into tension, and a tightening device that can be attached to the above-mentioned pin when the matrix tightener is already applied with the relative matrix around the tooth, so as to be capable of making it rotate while tightening the matrix and making it adhere to the outer walls of the tooth itself.

An example of device made in this way is provided by U.S. Pat. No. 4,396,374, for example.

The drawback that is encountered in the use of device of this type is that of the insufficient ease of handling: in fact it is necessary to first apply the matrix tightener and the matrix, with the matrix not yet in tension, while manually maintaining in position in the oral cavity, and then to insert the tightening device by attaching it the matrix tightener, while still manually holding the matrix, until it has been placed in tension. All this involves significant practical difficulties and a situation of prolonged discomfort for the patient.

The inventor of the present invention has attempted to eliminate this drawback by working out a unit including both a matrix tightener and a turnbuckle which can be made integral, so that the matrix can be applied, maintained in the correct position and tightened merely by inserting and subsequently activating the tightening device, which moves with itself the matrix which is integral with it.

Object of the Invention

The object of the invention is thus a unit comprising a matrix tightener and a tightening device for use in dentistry composed of a matrix tightener including a pin equipped with a slot for the introduction of the ends of the matrix and with a casing also equipped with slot, which holds the pin within itself, and with a tightening device that can be attached to said pin and capable of making the pin rotate, by the fact that the matrix tightener and the tightening device are equipped with means of attachment capable of making them integral in a reversible manner.

BRIEF DESCRIPTION OF THE DRAWINGS

A detailed description of the functioning of the invention as a unit according to some preferred embodiments will now follow, with reference being made to the attached drawings.

DETAILED DESCRIPTION OF THE INVENTION

Figure 1:
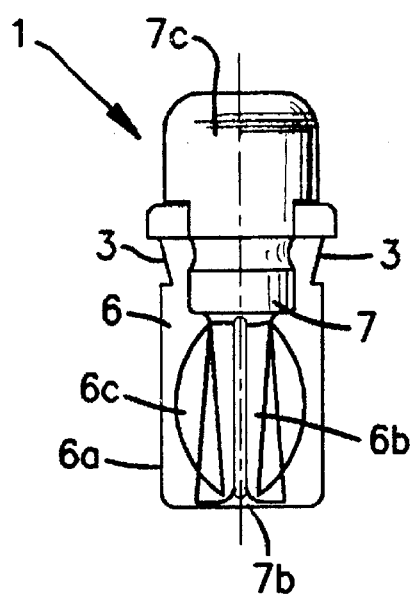
FIG. 1 represents an enlarged transparent view of an embodiment of the matrix tightener in the unit according to the invention.
Figure 2:
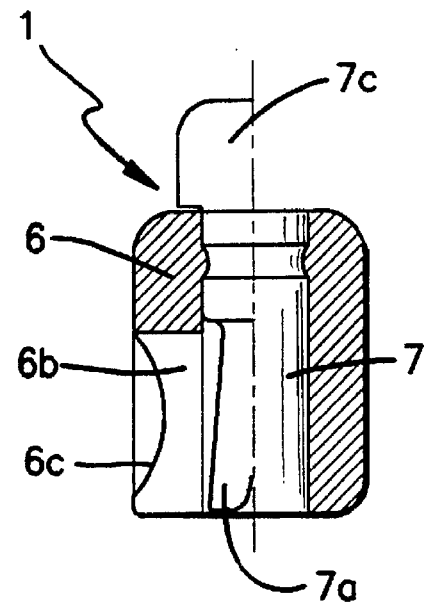
FIG. 2 represents one of its cross-sections.

When FIGS. 1 and 2 are studied, it should be noted how casing 6 of matrix tightener 1 in one embodiment includes, on the external wall that exhibits slot 6b for the introduction of the matrix, concave depression 6c shaped to essentially adapt itself to the wall of the tooth that is being operated on.

This depression, together with the fact that casing 6, in the present embodiment, is constructed of a material having properties of elasticity, makes it possible to make matrix tightener 1 adhere to teeth with various shapes in the best way possible.

Since pin 7 is made with a rigid material, it is slightly "forced" into casing 6 which, with its elasticity, ensures in time the necessary adherence between the two parts.

Figure 3:
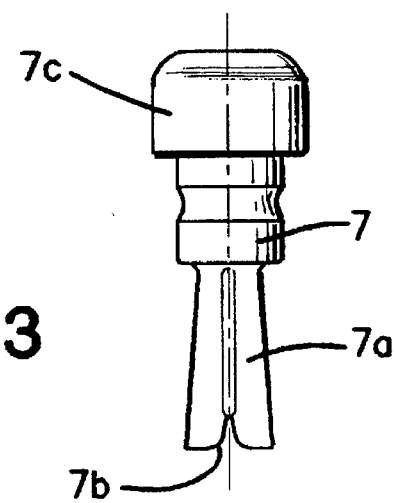
FIG. 3 represents the enlarged lateral view of only the pin of the above-mentioned matrix tightener, in which the teeth of the toothed member applied to one of its ends have not been drawn.
Figure 6:
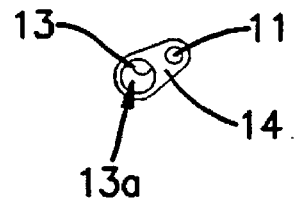
FIG. 6 represents a detailed view from which it is possible to deduce the position of the small connecting rod with two winches at that moment which contributes to effecting the blocking of the matrix tightener onto the tightening device in FIG. 5.
Figure 4:
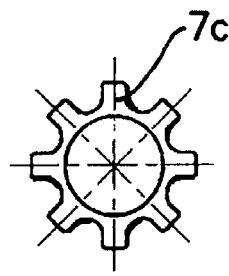
FIG. 4 represents the enlarged view from above of a preferred embodiment of the above-mentioned toothed member.
Figure 8:
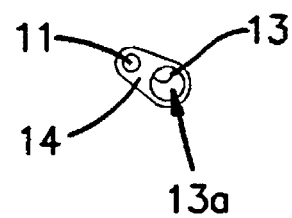
FIG. 8 represents a detailed view with the position of the above-mentioned connecting rod in the situation depicted in FIG. 7.
Figure 5:
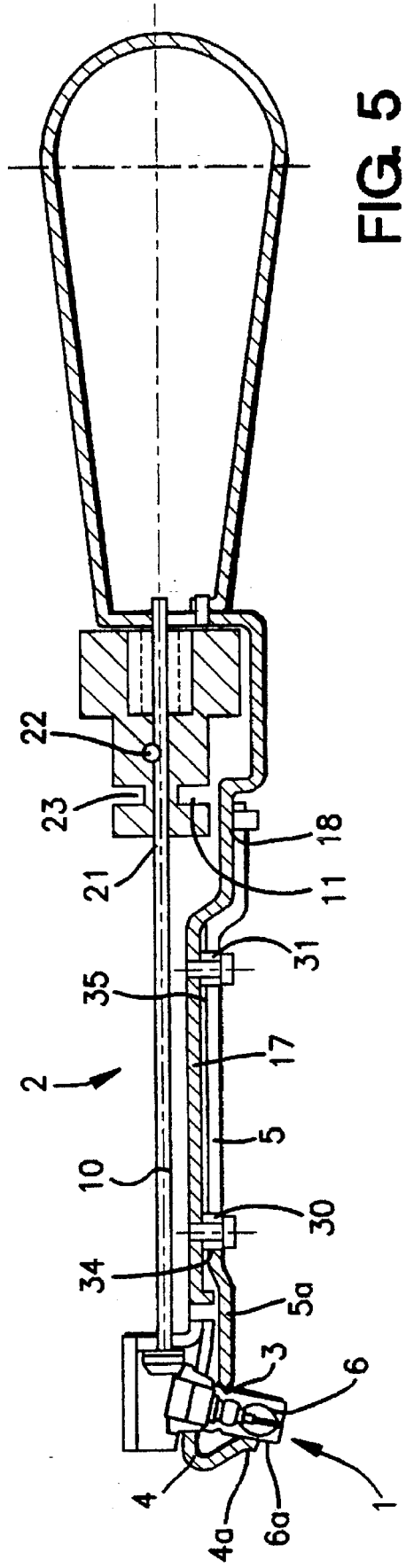
FIG. 5 represents the longitudinal section of an embodiment of the tightening device at the moment at which it is joined to the matrix tightener.
Figure 7:
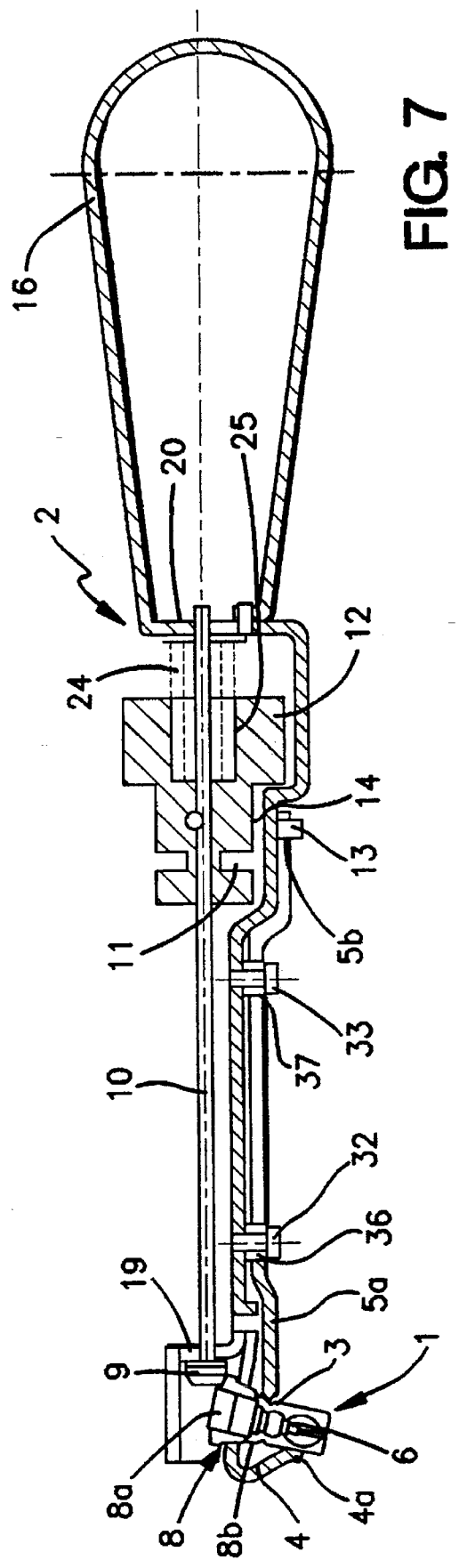
FIG. 7 represents the longitudinal section of the tightening device itself which it has been made integral with the matrix tightener, thereby constituting the unit according to the invention.

Again in FIGS. 1 and 2, and also in FIG. 3, it can be seen how pin 7 of matrix tightener 1 is moved by toothed wheel 7c and how it exhibits conical section 7a that converges toward the end that supports it.

Such a characteristic implies that, by one angle of rotation of its pin 7, the matrix undergoes increasing traction from its side that is closest to said toothed wheel 7c toward the other side that is in proximity to the base of the cone.

Since matrix tightener 1 is applied with above-mentioned toothed wheel 7c turned toward the crown of the tooth, the result that derives is that the matrix undergoes a greater traction corresponding to the cervical area of the tooth which normally has a circumferential development lower than that of the equatorial area, and thus it adheres with greater precision over the whole surface of the tooth.

As it can be seen from FIG. 1, casing 6 of the matrix tightener is square and exhibits pairs of parallel flat surfaces that face one another.

On at least one of these surfaces, but on two facing surfaces in the preferred embodiment represented, two grooves 3 are made so that two suitable shaped protruding members 4, 5 of the tightening device can grasp matrix tightener 1 by engaging respectively within groove 3 of one of the surfaces and against the flat surface, which functions as a reference surface of opposing surface 6a.

This task is accomplished by a pair of members 4, 5 FIGS. 5–8 of tightening device 2 of which one member 4 is shaped as a hook and exhibits flat area 4a with which it can be supported on the above-mentioned reference surface of one surface 6a of casing 6 and the other member 5, in laminar form, has an extremity 5a so as to be able to be engaged with above-mentioned groove 3 made on the opposing surface. These members 4, 5, once they have been engaged as said, function as pincers and make tension matrix 1 integral with tightening device 2 either while they are being applied in the oral cavity or while the matrix is being wound and tightened.

It has been pointed out that in the drawings the matrices have not been represented, since visualizing their position and shapes does not pose even the slightest problem for a person skilled in the art.

Of the two protruding members 4, 5 first member 4 that is shaped as a hook is equipped on its end with extension 17 of handle 16 of tightening device 2 and second member 5 is equipped on its extremity with laminar body 5 which is attached under above-mentioned extension 17 in such a way that it can move over a preset sliding course parallel to the extension.

Above-mentioned member 5 also has an oblong hole intended for the passing of winch 14, the function of which will be explained in the continuation of the present description.

Second protruding member 5, in the embodiment described, exhibits two oblong notches 30, 31 through which two fastening screws 32, 33 pass which are attached to above-mentioned extension 17 of handle 16 and are equipped with broadened heads to which spacers 36, 37 and washers 34, 35 are also applied which have a diameter greater than the width of oblong notches 30, 31 so as to be able to support second member 5 itself while it, thanks to said oblong notches, moves over a sliding course with respect to extension 17 of handle 16.

The above-mentioned sliding motion is transmitted to said second protruding member 5 by causing winch 14 mentioned earlier and that is equipped with two connecting rods 11, 13 attached to its ends to rotate.

One of these connecting rods 13 passes with slub 13a hole 18 placed on second protruding member 5, a hole in relation to which it is eccentric so that its rotation integral with connecting rod 14 causes the sliding that was described earlier (FIGS. 6, 8).

The other connecting rod 11 attached to the other end of winch 14 engages for a good part of its length into a toroidal groove 23 made on ratchet 12 that can be slid along coaxial shaft 10 parallel to the axis of extension 17 of handle 16, and thus parallel to the axis of device 2.

The sliding of ratchet 12 causes the rotation of winch 14 and, by means of connecting rod 13, the consequent movement of member 5.

The resulting sliding motion of the latter ends up parallel and consequently reduced to a preset extent, in relation to the shift of ratchet 12.

This ratchet exhibits on the inside along its axis a sliding hold equipped with protrusion 22 which is connected in a sliding manner with groove 21 made on one section of shaft 10 through which it passes coaxially, parallel as mentioned before to extension 17 of handle 16 and supported at its ends, free to be able to rotate, by two supports 19, 20, with one 19 located at the extremity of extension 17 itself and the other 20 located on one part of handle 16.

Between handle 16 and ratchet 12 there is then inserted, coaxially to shaft 10, compression spring 24 housed in housing 25 located in ratchet 12 itself.

It is clear at this point that, with the same hand that holds handle 16, an operator can slide ratchet 12 along its axis coaxially to shaft 10, causing, as explained earlier, second protruding member 5 to slide and, at the same time causing it rotate around its own axis, also bringing into rotation coaxial shaft 10 attached to it.

Spring 24 mentioned above then ensures the return of ratchet 12 to its original position.

At the extremity of above-mentioned shaft 10, besides support 19, conical toothed pinion 9 is fitted.

Corresponding to it, at the end of extension 17 of handle 16, there is also attached, free to rotate, member 8 comprising conical toothed wheel 8a and toothed crown 8b integral and coaxial with one another.

Conical toothed wheel 8a meshes with pinion 9 of shaft 10, and toothed crown 8b is sized to mesh with toothed wheel 7c of pin 7 of tension matrix 1 mentioned previously.

With the unit according to the invention it is thus possible, by maneuvering ratchet 12 merely with the hand that is holding tightening device 2, to carry out the following operations:

to shift second protruding member 5 so as to allow for the insertion of matrix tightener 1, by making it "mesh" with shaft 10; to allow the return of second protruding member 5 itself by means of spring 24 so as to make it go into groove 3 of casing 6 of matrix tightener 1 by pushing matrix tightener itself against flat part 4a of first fixed protruding member 4 so as to make tension matrix 1 and tightening device 2 integral with one another;

to apply matrix tightener 1 (which will have obviously been previously equipped with the relative matrix) to the tooth to be reconstructed;

to make pin 7 of matrix tightener 1 rotate by tightening the matrix;

to again displace second protruding member 5 so as to disengage end 5a of protruding member 5 of tightening device (from matrix tightener 1), thus removing the device from the oral cavity of the patient.

The practical and convenient features of these operations are evident which, as already said, reduce patient discomfort to the minimum.

As in the preferred embodiment described to this point, it is furthermore noted that, since toothed member 7c of pin 7 of matrix tightener is a toothed wheel, it may have, without any prejudice to the reliability of the attachment, dimensions that are much reduced in relation to those necessary given the present state of the art, something which involves a limited encumbrance of matrix tightener 1 and makes possible the simultaneous application of various matrix tightener to several adjoining teeth.

The inventors of the present invention have also worked out a further embodiment thereof which allows for even greater maneuverability of the unit according to the invention, particularly with respect to the operation of disengaging the matrix tightener and the matrix attached to it either from the tightening device or from the tooth on which the reconstruction work is being done.

The realization of the unit described up to this point, as said, in fact includes a tightening device capable of causing the pin of the matrix tightener to rotate to wind the matrix and to tighten it, as well as to unwind it, by causing it to rotate in the opposite direction, so as to disengage it from the tooth after the operation. However it has been observed that this rotation to be effected in both directions, especially in some cases, involves a certain degree of difficulty, especially in the final operation of disengagement, because of the inelastic deformation of the generally metallic material of the matrix due to its being wound around the above-mentioned pin.

With the embodiment that will now be described, this drawback has been eliminated by devising a unit of a different design that is adapted to effect a smooth immediate disengagement of the tightening device from the matrix tightener without the pin of the tension matrix having to rotate for a second time, as already mentioned, for the purpose of freeing the matrix and disengaging it from the tooth to which it was applied.

Figure 9:
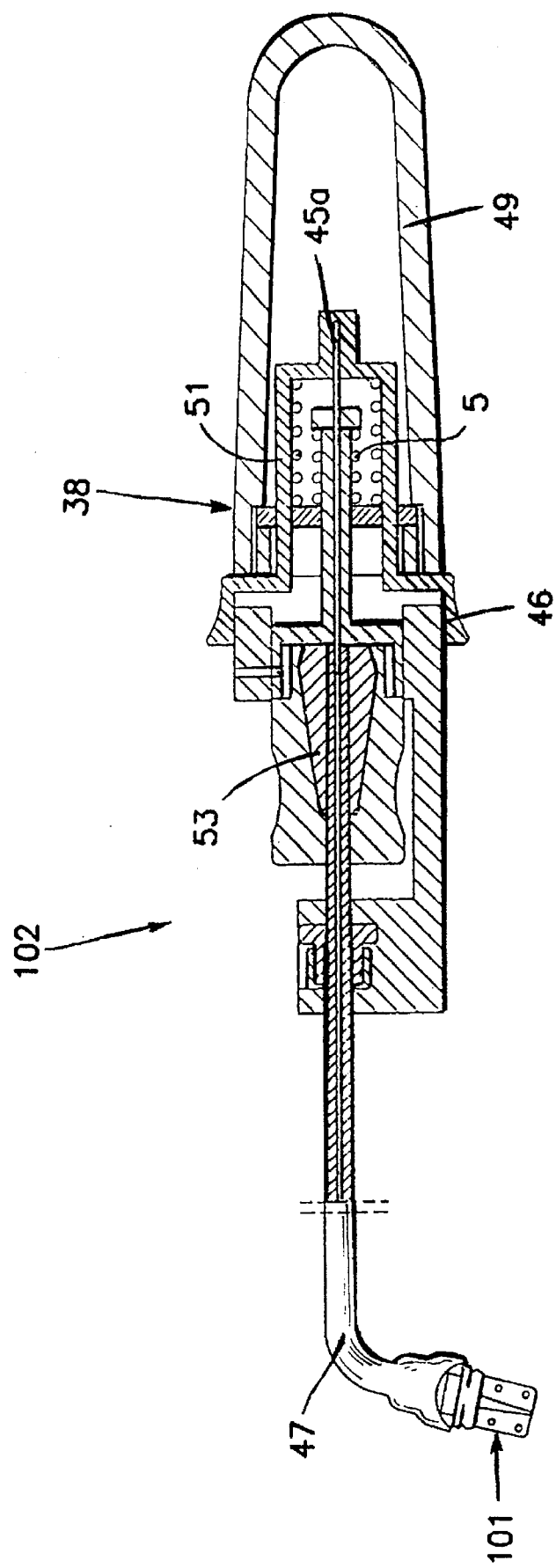
FIG. 9 represents another preferred embodiment of the unit according to the invention seen along a longitudinal section with the tightening device and the matrix tightener having been made integral with one another.
Figure 10:
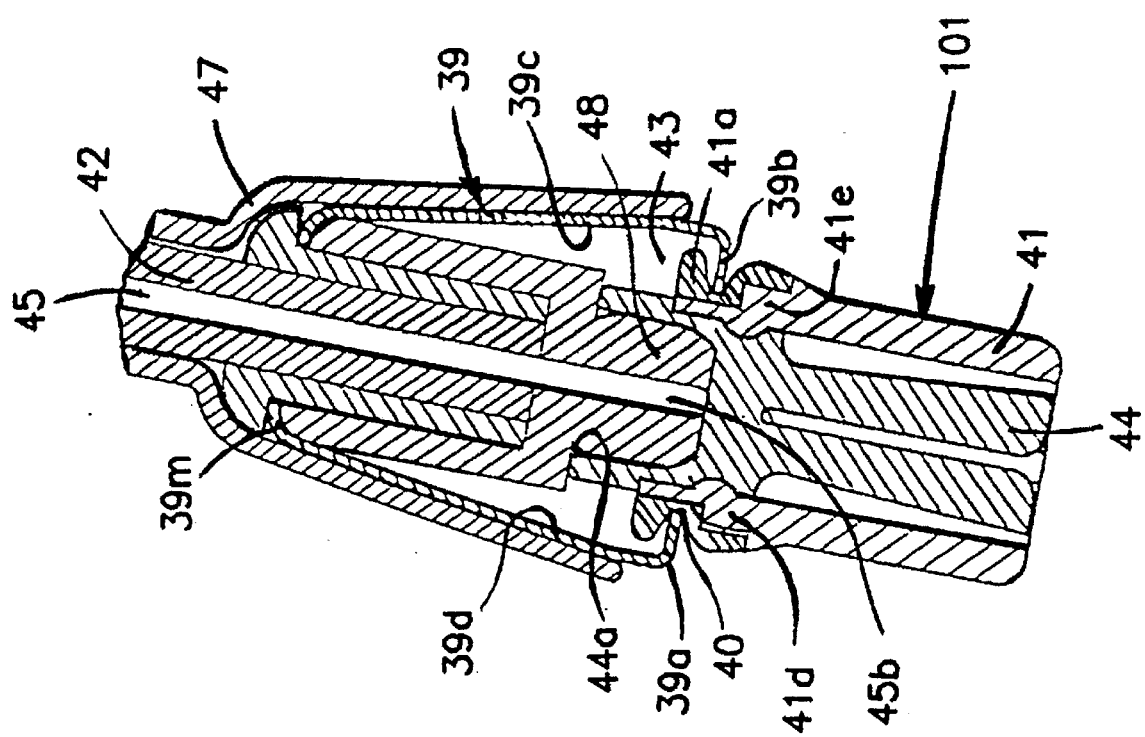
FIG. 10 represents the enlarged view of the area of joining between the matrix tightener and the tightening device in the embodiment of FIG. 9.

Observing FIGS. 9 and 10, it is seen how the connection that makes tightening device 38 and tension matrix 101 integral with one another is effected by means of flexible fork 39 which ends in protruding parts 39a, 39b and which, when it is inflected, connects in a reversible manner with shaped groove 40 located on part 412 attached to casing 41 of tension matrix 101.

In the present embodiment represented in the drawings, the inflection of fork 39 is obtained by exerting traction on it, by means of small flexible hollow cable 42, which causes it to be inserted within cavity 43 of part 47 of tightening device 38, capable under such conditions of holding it with its two sides 39c, 39d adhering against its internal walls.

This small flexible hollow cable 42 is attached at one end to middle part 39m of fork 39 and at the other end to activating member 53 attached to tightening device 38, which will be better explained below.

The part attached to casing 41 of tension matrix 101 with which fork 39 is connected is, in the present embodiment, ring 41a that contains within it, by means of slightly forced connection, two protrusions 41d, 41e symmetrical to one another and belonging respectively to two likewise substantially symmetrical parts 41f, 41g of casing 41 of matrix tightener 101 that face one another.

These two parts 41f, 41g (FIG. 12) are joined to each other along a vertical line H—H by means of the very material of which they are made; this material is chosen from among those that exhibit a sufficient degree of flexibility and elasticity and they are free to rotate in relation to one another, facing each other respectively to make up casing 41 and contain within them pin 44 or by moving away from one another freeing pin 44 and the matrix that is eventually attached to it.

This rotation, as can be understood, takes place precisely around line H—H which passes through their area of junction.

Therefore fork 39, as has been said, can be attached integrally to shaped groove 40 of above-mentioned ring 41a, making matrix tightener 101 integral with tightening device 38.

To ensure the rotation of pin 44 in an integral manner with flexible hollow cable 42, to cable 42 is attached body 48 having a shaped section so as to engage integrally in the rotation with a cavity 44a located on the "head" of pin 44.

Once the operation is finished, by exerting a thrust on pin 44 by means of flexible wire 45 placed coaxially within small flexible hollow cable 42 and which rests on pin 44 itself with one end 45b, while having other end 45a attached to activation member 46, it is possible to cause pin 44 to slide axially, unthreading it from ring 41a together with two above-mentioned parts 41f, 41g of matrix tightener 101 which are no longer held, which, for example, by the effect of a somewhat limited elasticity of the flexible material of which they are made, become half open thus leaving free pin 44 and the matrix attached to it, making it possible to disengage it smoothly from the tooth that has been treated.

Tightening device 38 capable of making possible the procedure that has just been described is composed of:

terminal elongated part 47 that is inclined in relation to the longitudinal axis of tightening device 38 itself and carrying cavity 43 capable of holding within itself above-mentioned fork 39;

small flexible hollow cable 42 placed coaxially within part 47 and attached, as said before, at one of its ends to middle part 39m of above-mentioned fork 39 and at its other end with a first activation member 53 of tightening device 38;

flexible wire 45 placed coaxially within above-mentioned hollow cable 42 and having one end 45b that rests against pin 44 which is attached, free to rotate, to casing 41 of matrix tightener 101, when this matrix is integral with the tightening device, and its other end 45a integral with second activation member 46 of tightening device 38.

Tightening device 38 includes handle 49 that is integral with above-mentioned long-shaped part 47, rotating ratchet 53 that is integral in its rotation and in its sliding with flexible hollow cable 45, and second activation member 46, free to slide in relation to handle 49, so as to slide the above-mentioned flexible wire 45 in relation to which it is integral.

Return springs 51, 52 then restore to its initial position activation member 46 after it has accomplished the above-mentioned sliding.

Figure 13:
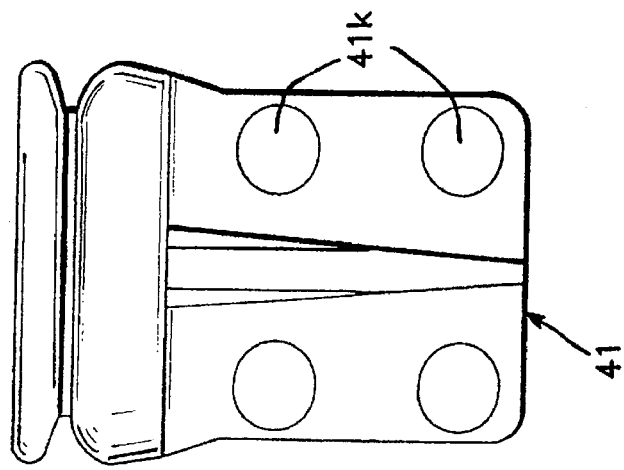
FIG. 13 represents the same matrix tightener seen in a lateral view.
Figure 12:
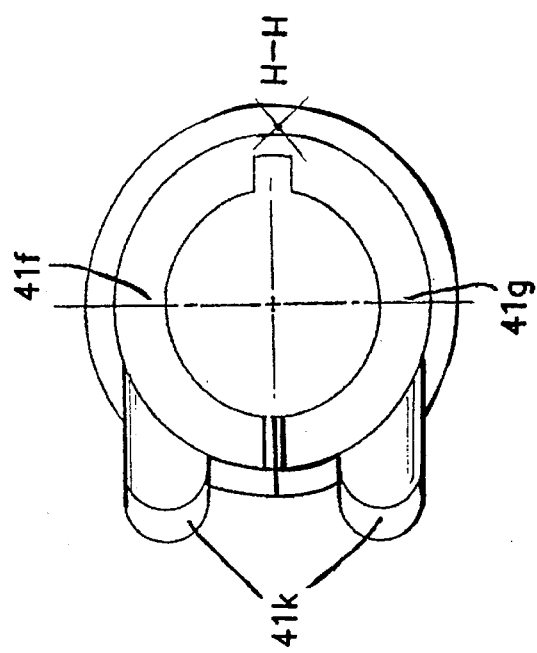
FIG. 12 represents the matrix tightener of FIG. 11 in a view from below.
Figure 11:
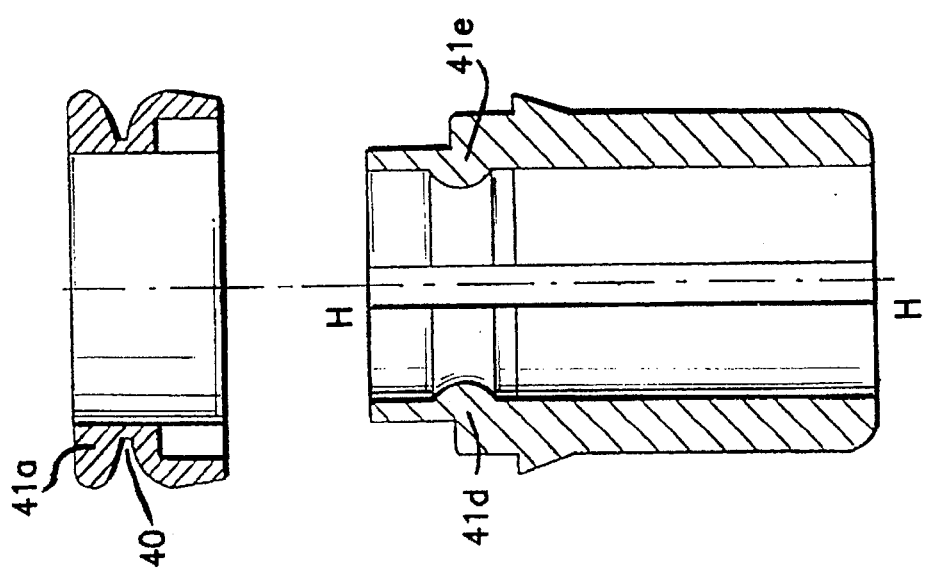
FIG. 11 represents a further embodiment of a particular type of matrix tightener that can be used in the unit of the invention seen in exploded view along a longitudinal section.

In FIGS. 11, 12, 13 an example of matrix tightener is represented that can be used in the unit; it is equipped with a plurality (four in the figures) of peduncles 41k that serve to distance casing 41 matrix tightener from the tooth, making possible the passage of the matrix.

The materials for the construction of the matrix tightener can be chosen from among the various types of materials and synthetic resins present on the market, with preference for those that endure temperatures higher than 120° C. so as to make it possible to sterilize the matrix tightener itself easily.

Other embodiments either of the tightening device or of the matrix tightener, that can be realized by an expert in the field according to the various requirements for use, are possible without going beyond the scope of the protection conferred by the attached claims. The examples that have been described and depicted are to be considered preferred embodiments of the unit according to the invention, neither binding nor limiting in particular with respect to the shape, the relative positioning and the sizing of the various component parts.

We claim:

1. In a dental matrix tensioner comprising a casing containing a pin rotatable relative to the casing, the pin having a slot therein for releasably receiving a dental matrix and for tightening the matrix about a tooth upon rotation of the pin relative to the casing, and means to rotate the pin relative to the casing; the improvement wherein the rotating means comprises an elongated assembly, and means movable lengthwise of and relative to the assembly in one direction to grip said casing and in an opposite direction lengthwise of and relative to the assembly to release said casing thereby selectively releasably to retain said rotating means in assembled relation with said casing.

2. A device as claimed in claim 1, wherein said lengthwise movable means also has a portion that is rotatable and is selectively engageable with said pin to rotate said pin upon rotation of said movable means.

3. A device as claimed in claim 2, wherein said lengthwise rotatable portion has a noncircular end which fits removably in a noncircular recess in said pin whereupon when said end is inserted in said noncircular recess and said portion of said lengthwise movable means is rotated, said pin is turned relative to said casing.

4. A device as claimed in claim 3, and further movable means movable lengthwise relative to the first-mentioned movable means into and out of contact with a bottom of said noncircular recess in said pin to assist in dislodging said noncircular end from said noncircular recess.

5. A device as claimed in claim 4, wherein said portion of said lengthwise movable means is a flexible cable and said further movable means is a wire slidable lengthwise within said cable.

6. A device as claimed in claim 1, wherein said lengthwise movable means comprises a pair of gripper members movable toward and away from each other respectively to grasp and release said casing, and cam means that move said members toward and away from each other upon said lengthwise movement.

7. A device as claimed in claim 6, said cam means comprising a pair of oppositely-inclined stationary surfaces on opposite sides of said gripper members, one of said surfaces engaging each of said gripper members.

* * * * *